United States Patent
Schacher

(10) Patent No.: US 8,562,909 B2
(45) Date of Patent: Oct. 22, 2013

(54) DEVICE FOR DECAPPING AND RECAPPING SAMPLE TUBES

(75) Inventor: Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/495,137

(22) Filed: Jun. 13, 2012

(65) Prior Publication Data

US 2012/0321516 A1 Dec. 20, 2012

(30) Foreign Application Priority Data

Jun. 20, 2011 (EP) .................................... 11170615

(51) Int. Cl.
G01N 21/00 (2006.01)

(52) U.S. Cl.
USPC .................. 422/63; 422/64; 422/65; 422/66; 422/509; 422/560; 422/561; 422/562

(58) Field of Classification Search
USPC ........... 422/62–68.1, 500, 509, 512, 560–562
See application file for complete search history.

(56) References Cited

U.S. PATENT DOCUMENTS

| | | | | |
|---|---|---|---|---|
| 5,455,006 | A * | 10/1995 | Aota et al. | 422/63 |
| 6,544,799 | B1 * | 4/2003 | Lewis et al. | 436/180 |
| 6,589,789 | B1 * | 7/2003 | Hubert et al. | 436/45 |
| 6,599,476 | B1 | 7/2003 | Watson et al. | |
| 7,421,831 | B2 | 9/2008 | Neeper et al. | |
| 7,556,777 | B2 * | 7/2009 | Victor | 422/560 |
| 7,867,444 | B2 * | 1/2011 | Testrut et al. | 422/65 |
| 7,947,225 | B2 * | 5/2011 | Itoh | 422/63 |
| 7,972,579 | B2 * | 7/2011 | Brunner | 422/560 |
| 7,985,375 | B2 * | 7/2011 | Edens et al. | 422/64 |
| 8,158,060 | B2 * | 4/2012 | Nagai et al. | 422/65 |
| 8,357,538 | B2 * | 1/2013 | Self et al. | 436/47 |

(Continued)

FOREIGN PATENT DOCUMENTS

| | | |
|---|---|---|
| DE | 29518548 U1 | 3/1996 |
| EP | 0497112 B1 | 8/1992 |
| EP | 2282212 A1 | 2/2011 |
| WO | 99/28724 A1 | 6/1999 |

OTHER PUBLICATIONS

English translation of DE 29518548 U1 filed Mar. 28, 1996, EFL-Entwicklung and Service fur Labortechnik GmbH, 12 pages.

(Continued)

Primary Examiner — Brian R Gordon
(74) Attorney, Agent, or Firm — Roche Diagnostics Operations, Inc.

(57) ABSTRACT

A decapping/recapping device for removing closures from sample tubes and for reclosing sample tubes with the same closures is presented. The device comprises individual closure holders, each holder comprising a passive closure gripper for holding a closure, at least one actuator for actuating the passive closure gripper when removing a closure from a tube or reclosing a tube with its respective closure and at least one tube gripper cooperating with the at least one actuator for biasing a tube and its closure away from each other when removing the closure and for biasing the tube and its closure towards each other when reclosing the tube. One actuator is coupled to one passive closure gripper of a closure holder when removing a closure from a tube or when reclosing a tube with its respective closure and is decoupled from a passive closure gripper when the closure holder is holding a closure.

17 Claims, 10 Drawing Sheets

(56) References Cited

U.S. PATENT DOCUMENTS

| | | | |
|---|---|---|---|
| 2003/0100125 A1* | 5/2003 | Pressman et al. | 436/177 |
| 2003/0223916 A1* | 12/2003 | Testrut et al. | 422/104 |
| 2006/0086065 A1 | 4/2006 | Tomalesky et al. | |
| 2006/0210432 A1* | 9/2006 | Victor | 422/63 |
| 2008/0050277 A1* | 2/2008 | Gueller et al. | 422/62 |
| 2008/0292501 A1* | 11/2008 | Sattler et al. | 422/68.1 |
| 2011/0286886 A1* | 11/2011 | Luchinger | 422/68.1 |
| 2012/0301359 A1* | 11/2012 | Kraemer et al. | 422/64 |

OTHER PUBLICATIONS

Extended European Search Report issued Oct. 12, 2011 in Application No. EP 11170615, 6 pages.

* cited by examiner

DEVICE FOR DECAPPING AND RECAPPING SAMPLE TUBES

CROSS-REFERENCE TO RELATED APPLICATIONS

This application is a continuation of EP 11179615.6 filed Jun. 20, 2011, which is hereby incorporated by reference.

BACKGROUND

The present disclosure generally relates to in vitro diagnostics devices for automatically removing closures from sample tubes and, in particular, to a decapping/recapping device for removing closures from sample tubes and for reclosing the same tubes with the same respective closures. The present disclosure also refers to a pipetting system and to an analytical system comprising the decapping/recapping device.

Coming from diverse healthcare facilities, biological samples such as blood samples usually arrive in the laboratories in different kinds of sample tubes with various closures. These are called primary sample tubes because they are used to collect the samples, e.g., by venipuncture.

There are instruments, which may process primary sample tubes without the need to remove the closure, i.e., by accessing the sample contained in the primary tube by piercing the closure with, for example, a pipetting needle. Not all closures are however suitable for this procedure and not all types of instruments and/or analysis allow this type of procedure. Some types of instruments and/or analysis require the primary tubes to be opened before samples are pretreated and/or analyzed. Therefore, such instruments should have an automatic decapper to automatically remove the closure from a primary tube.

Automating decapping of test tubes is complicated by the variety of available test tubes, which may vary in diameter, height, and, especially, the variety of available closures. Some closures have, for example, a thread for screwing on primary tubes. Another type of closure is a rubber stopper or cap, which may be removed by a pulling motion. The closures may also differ in their composition. They may be made of rubber, plastic, etc.

Decapping devices that can decap, i.e., remove closures from, all or most of these types of primary tubes have been developed and are available on the market. However, in decapping the tubes, care must be taken not to break the tubes, generally made from glass or plastic, and not to spill any of the sample. There is a further constraint that spills of the sample and any vapors should not be transmitted to other tubes in the instrument which would cause cross-contamination and interfere with the testing and analysis of the samples. Moreover bio-hazard is also an issue as samples are potentially infectious. Thus tubes and closures have to be processed and/or disposed securely.

Once a primary tube has been opened and once a volume of sample has been withdrawn from the tube for processing, it is often desirable to reclose the primary tube, for example, for safety reasons as mentioned above and, in any case, if samples have to be stored for a longer period of time in the event that a further analysis is later required.

One approach is to dispose the original closure after opening the primary tube and to reclose the primary tube with another standard or universal closure. This has the main advantage to make the various steps of opening, pipetting and reclosing more independent from each other. In this way, a primary tube can be opened by a decapping device, moved to a work cell where samples are pipetted and processed and then moved to a recapping device where they are reclosed with a new closure, wherein the process can start over again for another tube before the processing of the previous tube is completed. Another advantage is that recapping is made easier because standard closures of one type are used and if tubes need to be re-opened, decapping is also easier. A disadvantage, however, is that a new closure is introduced for each primary tube, thus increasing processing costs and waste volumes as well as the complexity of the recapping device, since the delivery of a new closure to the recapping device for each tube is needed.

Ideally, the same closure that is removed from a primary tube is used to reclose the same tube. Decapping/recapping devices able to remove a closure of any type and reclose the tube with the same closure after a volume of sample has been withdrawn are also known. This type of device however has the disadvantage that sample processing throughput can be compromised since all steps of opening, pipetting, closing and moving a tube need to be completed before the process can be repeated for another primary tube.

Therefore there is a need for a decapping/recapping device for removing closures from sample tubes and for reclosing the same tubes with the same respective closures in order to increase processing throughput of sample tubes and decrease processing costs.

SUMMARY

According to the present disclosure, a decapping/recapping device for removing closures from sample tubes and for reclosing the sample tubes with the same respective closures is presented. The decapping/recapping device comprises a plurality of individual closure holders, where each individual closure comprising a passive closure gripper for holding a closure and at least one actuator for actuating the passive closure gripper when removing a closure from a tube or reclosing a tube with its respective closure. The at least one actuator is coupled to the passive closure gripper of an individual closure holder when removing a closure from a tube or when reclosing a tube with its respective closure and is decoupled from the passive closure gripper when the individual closure holder is holding a closure. The decapping/recapping device further comprises at least one tube gripper cooperating with the at least one actuator for biasing a tube and its closure away from each other when removing the closure and for biasing the tube and its closure towards each other when reclosing the tube.

In accordance with one embodiment of the present disclosure, a pipetting system comprising the decapping/recapping device is presented.

In accordance with another embodiment of the present disclosure, an analytical system comprising the decapping/recapping device is presented.

Accordingly, it is a feature of the embodiments of the present disclosure to have a decapping/recapping device for removing closures from sample tubes and for reclosing the same tubes with the same respective closures in order to increase processing throughput of sample tubes and decrease processing costs. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
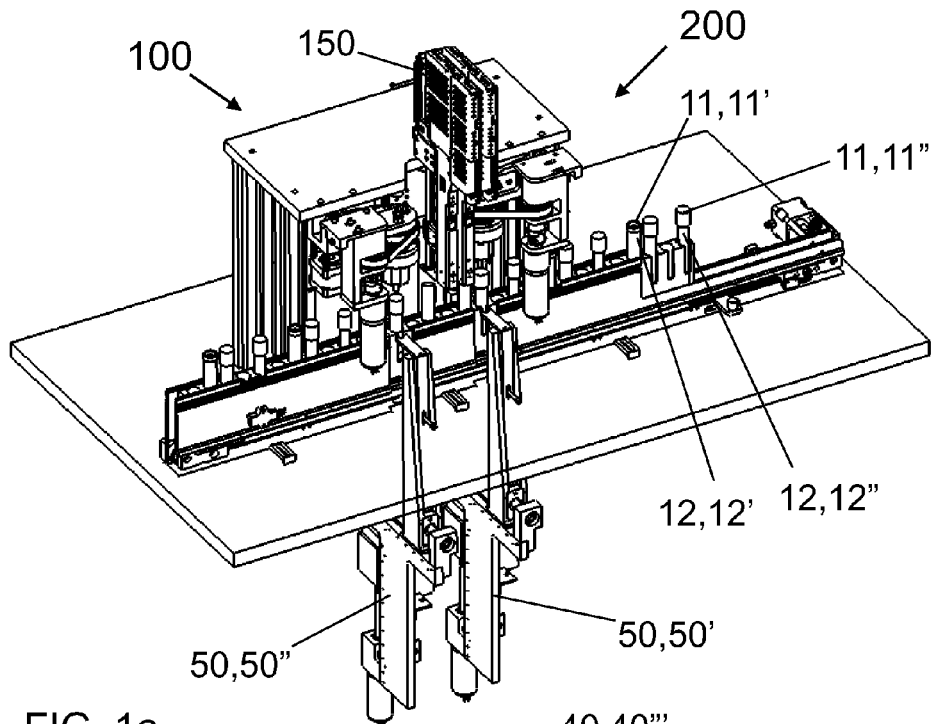
FIG. 1a illustrates a perspective view of a pipetting system comprising a decapping/recapping device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A "sample tube", herein interchangeably referred to also as "tube", can be either a sample collection test tube, also called "primary tube", which can be used to receive a sample such as a blood sample from a patient and to transport the sample contained therein to an analytical laboratory for diagnostics purposes, or a "secondary tube", which may be used to receive an aliquot of sample from a primary tube. A primary sample tube is typically made of glass or plastics, has a closed end and an open end closed by a closure, which may be of different materials, assume different shapes and colors, typically associated with the type of tube, i.e. the type of sample therein or the type of conditions the sample therein is subjected to. There are for example tubes containing an anticoagulant or a coagulation inducing agent, there are tubes containing gels facilitating the separation of plasma, etc. Different types of primary tubes are often just the result of customization of different primary tube manufacturers. Most often they reflect the type of sample and or analysis they are destined to. Primary tubes can be different size, i.e., of different diameter and/or different height for receiving different amounts of samples. A single laboratory, and typically a single instrument, can therefore be required to be able to handle different types of primary tubes with possibly different types of closures. A secondary tube can typically be made of plastics and may have a lower degree of variation of size and type with respect to primary tubes. In particular, secondary tubes may be smaller than primary tubes and be designed to be closed with one type or similar types of closure, e.g. a screw type.

The term "closure" is herein used to indicate any type of cap, comprising screw-type caps and rubber stoppers, which can be opened and/or closed by a pulling/pushing and/or screwing motion respectively.

A "decapping device" can be a device capable of automatically opening sample tubes of the same or different types by removing closures of the same or different types from their respective tubes.

A "decapping/recapping device" can be a device capable of automatically opening sample tubes of the same or different types by removing closures of the same or different types from their respective tubes and can be capable of automatically reclosing sample tubes with the same respective closures, which were removed from those tubes. Thus, a decapping/recapping device can be a decapping device, which additionally is adapted to reclose sample tubes with the same respective closures. A decapping/recapping device may also be used as a decapping device only. Therefore, unless otherwise specified, the general term "device" is hereafter used to indicate either or both a decapping device and a decapping/recapping device.

A device can comprise a plurality of individual closure holders, each comprising a passive closure gripper for holding a closure. A "closure holder" can be a device capable of holding a closure for a period of time between decapping, i.e. removal of that closure from a sample tube, and either disposal of that closure or recapping, i.e. reclosing of the same sample tube with that same respective closure. Each closure holder can comprise a passive closure gripper, a function of which is to securely hold a closure by a passive frictional pressure applied on the outer surface of a closure, preventing the closure to move and/or to fall. "Passive" can mean that there is a force or energy transfer between the passive closure gripper and other parts of the device, specifically an actuator, only when removing a closure from a sample tube or disposing a closure or reclosing a sample tube with its respective closure and there is no force or energy transfer between the passive closure gripper and the actuator during the period of time between decapping and disposal or recapping, the force required for holding the closure during this period of time being resilient and internal to the passive closure gripper itself. Thus, a closure gripper can be passive in the sense that it needs to be coupled with an actuator when decapping or recapping has to take place but cannot perform such actions without being coupled to an actuator.

An "actuator" can be a device for actuating, i.e. transferring force or energy to the passive closure gripper when removing a closure from a tube or reclosing a tube with its respective closure. The actuator can be coupled to a passive closure gripper of a closure holder when a closure has to be removed from a tube or when a tube has to be disposed or reclosed with its respective closure and being decoupled from a passive closure gripper when the closure holder is holding a closure. According to one embodiment, the force can be an axial force, transferred to the passive closure gripper by applying a positive or negative pressure, e.g. by pushing or pulling a passive element of the passive closure gripper. The force may also or in addition be rotational, transferred to the passive closure gripper by coupling to rotational drive means. The force may be however also induced, i.e. without physical contact, e.g. magnetic.

"Coupled to" or "in coupling connection", when referring to the relationship between an actuator and a passive closure gripper, can mean that an actuator is engaged with a passive closure gripper and a transfer of force from the actuator to the passive closure gripper is enabled. Engagement may occur by physical contact and/or alignment. "Decoupled from" can mean that the actuator and the passive closure gripper are disengaged, i.e. physically separated from each other or misaligned. Alternatively, the actuator and the passive closure gripper may still be in physical contact or aligned but the transfer of force from the actuator to the passive closure gripper is disabled, meaning that there is no force or energy transfer from the actuator to the passive closure gripper.

Therefore, it is thus possible to couple a plurality of closure holders to one or more actuators. According to one embodiment, one or more actuators are fixed within the device while a plurality of closure holders are movable with respect to the fixed actuators such as to be in turn coupled to one or more actuators. Of course the opposite can also be possible, wherein a plurality of closure holders is fixed and one or more actuators are movable with respect to the fixed closure holders.

The device can further comprise at least one tube gripper cooperating with the at least one actuator for biasing a tube and its closure away from each other when removing the closure and for biasing the tube and its closure towards each other when reclosing the tube. According to one embodiment, the at least one tube gripper can be aligned with the at least one actuator. If there are a plurality of actuators and a plurality of tube grippers, two or more tube grippers may be aligned with a respective number of actuators. According to one embodiment, the tube gripper can lift and hold a tube with respect to a closure holder coupled to an actuator wherein the actuator cooperates with the tube gripper to remove a closure from the sample tube or reclose the tube with its original closure held by the closure holder. It is however also possible to adapt the device such that the tube gripper can hold a sample tube without lifting it while the closure holder and/or the actuator are moved with respect to the tube gripper. Alternatively, the tube gripper and the closure holder and/or the actuator can move with respect to each other.

According to one embodiment, the closure gripper can comprise a gripping tool and a pre-tensioning member connected to the gripping tool, such as a spring, pre-tensioning the gripping tool with respect to the closure holder in one pivoting direction (closing direction) for exercising a pressure on the sides of a closure symmetrically arranged in between, wherein the pressure is releasable upon coupling the actuator to the passive closure gripper by a force applied by the actuator on the pre-tensioning member. The closure is preferably held hanging by the gripping tool without touching other surfaces or parts of the device until disposed or returned to its respective sample tube.

According to one embodiment, the gripping tool can comprise a plurality of jaws symmetrically arranged with respect to a central vertical axis of the closure holder, each jaw comprising a friction surface, preferably a plurality of protrusions, e.g. conical protrusions, preferably arranged in a two-dimensional array, the jaws cooperating with each other to grip and hold a closure.

This embodiment can particularly be advantageous for removing and holding closures of variable shape and material and also for reclosing sample tubes with the closures since the maximum gripping power with the minimum contact surface can be achieved. In this way, a closure can be held firmly without falling during holding or sliding through the jaws during decapping or recapping. Moreover, asymmetrical deformations of the closure are prevented for smooth and efficient decapping and recapping. Also, only a minimum contact between the gripper and the outer sides of the closure takes place, thus minimizing the risk of cross-contamination from one closure to the next closure due to possible sample traces present on the inside and/or bottom surface of the closure. According to one embodiment, each jaw can pivot about a horizontal jaw axis by varying its angle relative to the central vertical axis of the closure holder. This can enable the jaws to adapt to different inclinations of the sides of the closure without losing gripping surface and power.

According to one embodiment, the closure holder can comprise a passive closure push element, independent from the gripping tool, comprising a resilient member, e.g. a spring, for exercising a push force on the closure in a vertical direction when the pressure of the gripping tool is released. The push element may be advantageously mounted above the gripping tool, e.g. the jaws. In this way, upon inserting a closure in the space between the gripping tool, e.g. by lifting a closed sample tube towards the closure holder, the push element can be pushed upwards by the closure and the resilient member can be tensioned. The resilient force of the resilient member is chosen such that it is weaker than the resilient force of the pre-tensioning member. Therefore as long as the closure remains tight held by the gripping tool, during the holding period, the push element is limited to exercise only a pressure on the top of the closure without additional effects. In the event that a closure is returned to a sample tube, during reclosing, the effect of the push element is also marginal, even though it may contribute to the closing. In the event that a closure needs to be disposed by releasing the pressure of the gripping tool, e.g. by opening the jaws upon coupling with the actuator, and allowing the closure to fall by gravity, it may occasionally happen that a closure remains stuck or that a closure gripper remains jammed. The push element can thus be advantageously designed for contributing to expel the closure by pushing it out from the closure holder. The push element may be however designed for exercising an additional effect, especially on certain types of closures such as rubber stoppers having a concave shape, i.e. a cavity, on the top of the closure. In this case, if the push element is shaped such as to fit at least in part in the cavity of the closure, asymmetrical deformation and/or tilting of the closure may be prevented when gripping the closure by the gripping tool. This can enable proper decapping and recapping of the sample tube.

According to one embodiment, the closure gripper can rotate about the central vertical axis of the closure holder upon coupling the actuator to the passive closure gripper. The actuator can comprise a closure-gripper drive for rotating the closure gripper. Rotation may be necessary for threaded screwable closures. Rotation may however be advantageous for other types of closures as well, not necessarily requiring screwing. According to one embodiment, the closure gripper is rotated thus rotating the closure with respect to the tube, while the tube gripper maintains the tube stationary. Alternatively, it is possible to rotate the tube while maintaining the closure stationary between the gripping tool.

According to one embodiment, the device can comprise a closure-holder drive for sequentially and/or repeatedly bringing the plurality of closure holders in coupling connection with one or more actuators and/or a tube conveyor for bringing one tube at a time in gripping alignment with a tube gripper.

According to one embodiment, the device can comprise a decapping station where a decapping actuator can be aligned to a decapping tube gripper, a recapping station where a recapping actuator can be aligned to a recapping tube gripper, wherein a closure holder and a tube are movable from the decapping station where the decapping actuator and the decapping tube gripper cooperate with the closure gripper to remove a closure from the tube, to the recapping station wherein the recapping actuator and the recapping tube gripper cooperate with the same closure gripper holding the closure to reclose the same tube with the same closure. The decapping and recapping actuators may be structurally identical but have different dedicated functions, i.e. for decapping and recapping respectively. They can be coupled to and actuate the same passive closure gripper but may be more specifically adapted for either decapping or recapping, for example by setting the closure-gripper drive to rotate a passive closure gripper clockwise or counterclockwise.

According to one embodiment, the plurality of individual closure holders can be arranged on a translatable linear array or a rotatable rotor-like array or a robotic arm-like transportation unit, with possible random access to any actuator. According to one embodiment, the plurality of closure holders can be symmetrically arranged on a carousel-type rotor comprising a plate or branches rotatable about a central rotor axis. The closure-holder drive may comprise in this case a motor driving the carousel in a controlled manner about its axis via e.g. a belt-pulley or gear-like mechanism or induction like mechanism. The rotor may comprise a position sensor for controlling and/or monitoring the angle of rotation such as to facilitate a proper alignment between actuator and closure holder at every rotation.

Sample tubes may be moved with respect to the device, particularly with respect to a decapping and/or recapping station, with a tube conveyor. Sample tubes can be carried on tube carriers, which may be either single tube carrier, so called "Pucks", or multi-tube carriers, so called "tube racks", comprising a plurality of tube receptacles for receiving e.g. up to 5 tubes or more and typically adapted to receive different types of tubes, i.e. of variable diameter and height. The tube conveyor may therefore comprise a transportation unit, such as a transportation band or guide rail driven by a motor and arranged such that a tube carrier is moved stepwise for bringing a tube at a time in alignment with a decapping and/or recapping station. The transportation unit may however be adapted to move tubes on special tube carriers customized according to the requirements of a decapping/recapping device and confined in the working area of the decapping/recapping device. In this case, a reformatting device for transferring sample tubes from pucks and/or tube racks to these special carriers and vice versa may be operatively coupled to the decapping/recapping device. Closure-holder drive means and tube conveyor can be synchronized to bring a tube and its closure to the same recapping station after the closure has been removed at a decapping station.

According to one embodiment, the device can comprise a height determining detector cooperating with the tube gripper for determining the height at which a tube is to be lifted when removing a closure from a tube or reclosing the tube with its closure. The height determining detector may be for example a code reader for reading a code placed on a tube or a tube carrier and identifying the type of tube or rack, e.g. a bar code reader or an RFID reader. The height determining detector may also be optical, comprising e.g. a camera-type detector or other light sensor adapted to measure geometrical parameter of the sample tubes and/or closures, particularly the height and/or the diameter of the tube and/or the size and shape or color of the closure. The height determining detector may be set up to send a signal to the tube gripper either directly or via a control unit. In this way the variability of the sample tube type is taken into consideration and each sample tube is lifted according to its respective geometric parameters, enabling its closure to be gripped and removed or enabling the tube to be reclosed with its closure held by the closure holder.

According to one embodiment, the tube gripper can comprise a first tube gripping tool and a second tube gripping tool. The first tube gripping tool can be biasable with respect to the second gripping tool and can cooperate with the second tube gripping tool such as the first tube gripping tool grips and can lift a tube from a tube carrier before the second gripping tool grips and holds securely the tube with a force and a surface of contact which are greater than the force and surface of contact of the first gripping tool respectively. This double gripping mechanism enables gripping the side wall of a tube in the often narrow space between a tube carrier and a closure with a smaller gripper means and to lift it to a height wherein a larger and stronger gripping tool can grip a longer portion of the side wall for a more secure grip.

According to one embodiment, the device can comprise an error detector comprising a sensor and a controller to determine whether a closure has been removed and/or a tube has been reclosed with its respective closure and/or to prevent a tube from being reclosed with a non-respective closure. The error detector may be the same, similar or share components with the height determining detector. The error detector may comprise an optical detector, e.g. a camera-type detector or other light sensor adapted to measure geometrical parameters and/or the presence or absence of a closure on a respective sample tube and/or in a closure holder. The error detector may be set up to compare a closed sample tube before decapping and after recapping. In the event of any error in the decapping/recapping process, it may emit a warning or alert signal to interrupt the decapping/recapping process and/or to instruct the device to dispose a closure which failed to reclose a sample tube before it is accidentally brought in contact with other closures or other sample tubes. Further, it may send instructions to process sample tubes left open or tubes, which failed to be opened, differently from the rest of the tubes.

According to one embodiment the device can comprise a waste station where a waste actuator is aligned to a waste compartment. A closure holder can move from a decapping station where a decapping actuator and a decapping tube gripper cooperate with the closure gripper to remove a closure from the tube to the waste station. The waste actuator cooperates with the same closure gripper holding the closure to dispose the closure into the waste compartment. Alternatively or in addition, the closure holder may move from a recapping station where a recapping actuator and a recapping tube gripper cooperate with the closure gripper to reclose a tube with its respective closure, to the waste station. This may happen in the event that an error occurred when trying to reclose the tube and the closure remained in the closure holder. In order to free the closure holder and make it available for another closure from another tube and/or to prevent that a different tube is closed with a closure that does not belong to that tube, the closure is therefore disposed at the waste station before the closure holder is returned to a decapping or recapping station.

According to one embodiment, the device can comprise at least one decapping station and at least one waste station. According to one embodiment, the device can comprise at least one decapping station and at least one recapping station. According to one embodiment, the device can comprise at least one decapping station, at least one recapping station and at least one waste station. In all of these embodiments, a plurality of closure holders can move from one station to another station by being coupled to a respective actuator. It is however possible that a closure holder only passes by a station without being coupled to an actuator. This may be for example the case if the closure holder is moved from a decapping station to a recapping station via a waste station. As there is no intention to dispose the closure because it is intended to reclose its respective tube at the recapping station, there will be no coupling between the actuator and the passive closure gripper at the waste station unless an error in the intended process was detected.

A pipetting system for withdrawing volumes of samples from sample tubes and/or dispensing a volume of another liquid, such as a reagent or diluting buffer, into a sample tube or reaction vessel can comprise a decapping/recapping device and a pipetting unit adapted, e.g. synchronized with the decapping/recapping device, to withdraw a volume of sample or dispense a volume of liquid in the time frame between the opening of a tube and the reclosing of the tube with the same closure. The pipetting unit may comprise one or more reusable washable needle, e.g. a steel needle, or use disposable pipette tips. The pipetting unit may be mounted to a transfer head that can be moved in one or two directions of travel in a plane, e.g. with guiding rails and a third direction of travel orthogonal to the plane, e.g. with a spindle drive.

The pipetting system can comprise a pipetting station where the pipetting unit, such as the pipette tip or needle, can be aligned with an open tube between decapping and recapping. The pipetting station may comprise a pipetting tube gripper similar or identical to a decapping or recapping tube gripper for lifting the tube such as access of the pipetting unit to the sample therein is facilitated. According to one embodiment, the pipetting station can be located between the decapping and recapping station in a path of travel of a tube carrier between the decapping station and the recapping station.

In a system that operates with single tube carriers, the decapping station and the reacapping station can be located at a distance from each other, which can correspond to the distance between the center of a tube and the center of a second apart tube in a series of tubes whose carriers are adjacent to each other. The pipetting station can be located in the middle, i.e. in correspondence to a tube in between. In one embodiment, the number of closure holders can be three. In this way a cycle may be defined wherein in a same fixed time frame, three tubes may be processed and three different steps may be performed. A first tube may be opened while a volume of sample can be withdrawn from or a volume of liquid is being dispensed into a second tube previously opened while a third tube, from or into which a volume of liquid has been previously withdrawn or a volume of liquid has been previously dispensed, can be reclosed with the same closure that in the same time frame has been transported by one of the closure holders from the decapping station to the recapping station. The cycle can then start over again.

In a system that operates with tube racks, the decapping station and the reacapping station can be located at a distance from each other, which can correspond to the distance between the center of a tube in the first receptacle of a first tube rack and the center of a first tube in the first receptacle of a second tube rack adjacent to the first tube rack. This can be advantageous if the distance between the centers of two tubes on the same rack is not the same as the distance between the center of the last tube and the center of the first tube respectively on adjacent racks. The pipetting station can also be located approximately in the middle, i.e. between decapping station and recapping station in correspondence to one of the intermediate tube positions. In one embodiment, if the tube racks comprising five receptacles for receiving a respective number of tubes, the number of closure holders can be six. In this way a cycle may be defined wherein three tubes may be processed and three different steps may be performed in a same fixed time frame. A tube on a rack, e.g. the first tube, may be opened while a volume of liquid is being pipetted from or into one of the tubes in a preceding rack previously opened while another tube, e.g. the first tube on the preceding rack, from which or into which a volume of sample has been previously pipetted, can be reclosed with the same closure that in the same time frame has been transported stepwise by one of the six closure holders from the decapping station to the recapping station.

A method of pipetting samples from sample tubes with the pipetting system can comprise opening a tube by removing the closure from the tube at a decapping station, withdrawing a volume of sample from the open tube and/or dispensing a volume of liquid into the open tube by the pipetting unit at a pipetting station and reclosing the tube with the same closure at a recapping station.

According to certain embodiments, the method can comprises performing in the same time frame opening a first tube by removing a first closure from that first tube at a decapping station, closing a second tube with a second closure removed from that same second tube at a recapping station, and withdrawing a volume of sample from an opened tube or dispensing a volume of liquid into an opened tube at a pipetting station, disposing a closure at a waste station.

The term "time frame" is here used to indicate a predetermined time window, e.g. in the range of a few seconds, e.g. 1 to 10 seconds, which defines a cycle during which at least two of the above mentioned steps take place either sequentially or in parallel or in overlap.

According to one embodiment, the method can comprise moving a tube and its closure independently from each other but in a synchronized manner from a decapping station, where the closure is removed, to a recapping station, where the tube is reclosed with the same closure, and pipetting a volume of sample from the opened tube and/or dispensing a volume of liquid into the opened tube in the time frame between decapping and recapping. According to certain embodiments, closures can be moved from a decapping station to a recapping station following a path of travel which does not overlap with the path of travel of the sample tubes except at the decapping station and recapping station. Analogously, according to certain embodiments, the pipetting unit can move following a path of travel, which does not overlap with the path of travel of opened sample tubes, except at the pipetting station. In this way, it can be prevented that samples in opened tubes are contaminated by eventual droppings from the closures while being held by a closure holder or from the pipetting unit.

Alternatively or in addition, the device may comprise a plate or shield located underneath the path of travel of the closure holders to protect other parts of the device from eventual droppings from closures held by the closure holders. Also, when cross-contamination is of particular concern such as when samples are used for nucleic acid amplification, other or additional measures may be implemented such as separating parts of the device in different compartments or enclosing the device or device parts in an aerosol free compartment such as a hood.

An analytical system for determining at least one sample parameter of a sample contained in a sample tube can comprise a decapping/recapping device and an analytical unit for determining the at least one sample parameter, such as a physical, chemical or biological parameter of a sample contained in a sample tube, normally without the addition of a reagent, in the time frame between the opening of a tube and the reclosing of the tube with the same closure. The analytical unit may be for example a sensor for determining a physical parameter of the sample, such as pH, temperature, colour, turbidity, viscosity, or quantity, e.g. volume, or liquid level of the sample within the tube. It may comprise for example an optical detector or a probe to be dipped at least partially into the sample. It may e.g. determine chemical or biological parameters such as analytes contained in the sample by photometric measurement or other physical techniques making use for example of ion selective electrodes or reagent coated strips subject to colour change, etc. The analytical system may further comprise a pipetting unit as above described.

A method of determining at least one sample parameter of a sample contained in a sample tube with the analytical system can comprises opening a tube by removing the closure from the tube at a decapping station, determining at least one sample parameter by the analytical unit and reclosing the tube with the same closure at a recapping station.

The same analytical unit may of course determine at least one sample parameter without the need to open a tube, e.g. before decapping and/or after recapping, especially if an optical detector is used.

A system for processing sample tubes comprising biological samples can comprise a plurality of work cells for processing samples and optionally at least one transportation unit to transport sample tubes from one work cell to at least another work cell. The system can further comprises a pipetting system in correspondence to at least one work cell for withdrawing a volume of sample from a sample tube to be processed by the work cell or dispensing a volume of liquid into the sample tube. The pipetting system can comprise a decapping/recapping device for removing a closure from a sample tube when a sample needs to be withdrawn or a liquid needs to be dispensed and for reclosing the sample tube before it is transported to another work cell.

A work cell can be either a stand-alone apparatus or a module within a larger instrument assisting users with the detection, e.g. qualitative and/or quantitative evaluation of samples for diagnostic purpose, or with the sorting and/or preparation of samples before detection, or with the storing and/or disposal of samples after detection. A work cell may be related to analytical and/or to pre-analytical and/or to post-analytical sample processing steps. Work-cells may connected to each other and depend at least in part on each other, e.g. each carrying out a dedicated task of a sample processing work-flow, which may be a prerequisite before proceeding to the next work-cell. Alternatively, work cells may work independently from each other, e.g. each carrying out a separate task, e.g. a different type of analysis on the same sample.

An analytical work cell can be either a stand-alone apparatus or module within a larger instrument assisting users with the detection, e.g. qualitative and/or quantitative evaluation of samples for diagnostic purpose. It may comprise a process and detection system whose workflow can be optimized for certain types of analysis. Examples of such work cells are clinical chemistry analyzers, coagulation chemistry analyzers, immunochemistry analyzers, urine analyzers, used to detect the result of chemical or biological reactions or to monitor the progress of chemical or biological reactions. An analytical work cell may comprise units assisting with the pipetting, dosing, mixing of samples and/or reagents. The work cell may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a reaction vessel or cuvette feeding unit. It may comprise one or more liquid processing units, such as a pipetting unit, to deliver samples and/or reagents to the reaction vessels. The pipetting unit may comprise a reusable washable needle, e.g. a steel needle, or disposable pipette tips. The work cell may further comprise one or more mixing units, comprising e.g. a shaker to shake a cuvette comprising a liquid or a mixing paddle to mix liquids in a cuvette or reagent container.

A pre-analytical work cell can be either a stand-alone apparatus or module within a larger instrument assisting users with the sorting and/or preparation of samples before being processed by an analytical work cell. It may comprise for example one or more of the following: a resorting unit to sort samples according to type of analysis and/or priority of analysis, a centrifuge for centrifugating sample tubes, an aliquoting unit wherein a pipetting unit is used to aliquot samples from sample tubes, a thermal treatment unit to subject the sample to a certain temperature, a separation unit to separate sample components, etc.

A post-analytical work cell can be either a stand-alone apparatus or module within a larger instrument assisting users with the storing and/or disposal of samples after being processed by an analytical work cell. It may comprise for example a resorting unit to resort sample tubes, e.g. to different storage racks, and/or a refrigerated compartment.

In general, a work cell may comprise units for loading and/or unloading and/or transporting and/or storing sample tubes or racks comprising sample tubes, units for loading and/or unloading and/or transporting and/or storing reagent containers or cassettes, units for loading and/or unloading and/or transporting and/or storing and/or washing reaction containers, e.g. cuvettes. The reaction containers may be disposable, i.e. single use, or reusable, i.e. adapted to be washed and reused. It may comprise identification units comprising sensors, e.g. barcode or RFID readers. A work cell may also comprise one or more incubation units for maintaining sample/reagent mixtures at a certain temperature during reaction, wash stations for washing pipette tips or needles, mixing paddles, etc.

As each work cell may be designed for processing a certain number of samples or sample tubes per time unit, and this number may vary, the system may be advantageously set up such that the number of closure holders and/or the number of actuators and/or the number of tube grippers and/or the number of pipetting units is adapted to the throughput of each work cell.

Also, as each work cell may process only or preferably either sample tubes on single carriers or on racks carrying a plurality of tubes, each decapping/recapping device may advantageously process sample tubes transported on either single tube carriers and/or racks carrying a plurality of sample tubes.

According to one embodiment, the system can comprise a transportation unit for automatically transporting sample tubes from one work cell to another work cell. The transportation unit may also transport single carriers or tube racks or both. The transportation unit may comprise e.g. one or more transport lines arranged e.g. as transport bands or guide rails. The transportation unit may be connected to, e.g. be an extension of, the tube conveyor of various decapping/recapping devices. Bypass lines and/or junctions may also be present so that specific work-cells may be accessed in a random-access manner, by delivering the right sample to the right work-cell at the right time, according to need or priority and/or according to the type of tube or tube carrier, and not necessarily sequentially. The transportation unit may alternatively comprise a series of autonomous robotic carriers with random access to any work cell.

Alternatively, sample tubes and/or tube carriers may be transported from one work cell to another work cell manually by the user.

Figure 1B:
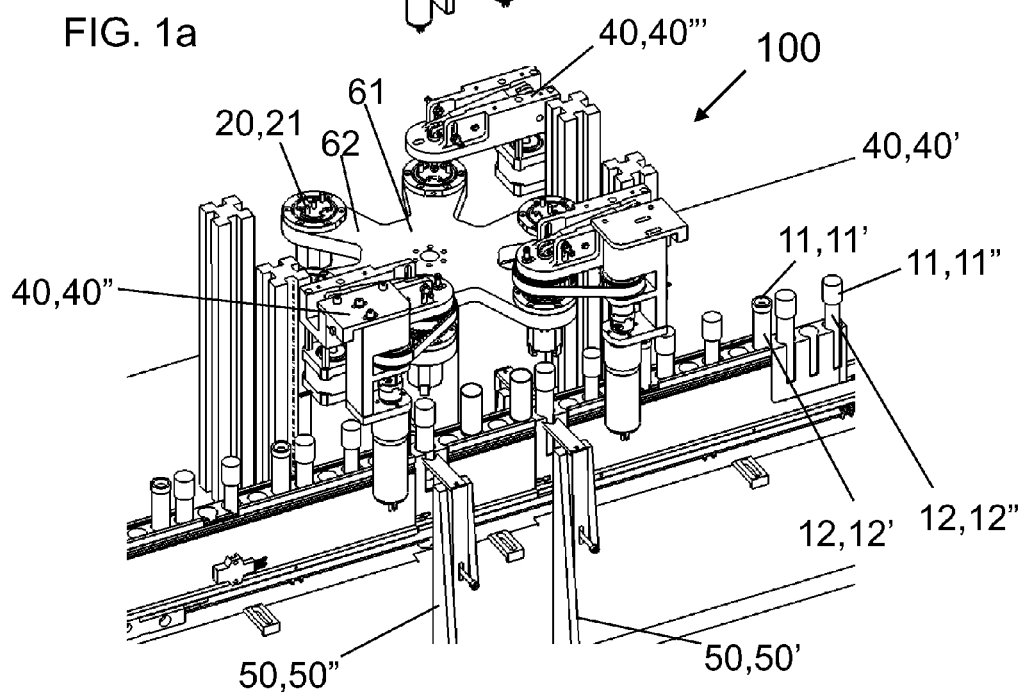
FIG. 1b illustrates a magnification of the decapping/recapping device shown in FIG. 1a wherein some parts have been removed for clarity according to an embodiment of the present disclosure.

Referring initially to FIG. 1, FIG. 1a shows a pipetting system 200 for withdrawing volumes of samples from sample tubes 12 and/or dispensing volumes of liquid into sample tubes 12 according to one embodiment. The pipetting system 200 can comprise a decapping/recapping device 100 (more clearly illustrated in FIG. 1b), for removing closures 11 of variable type 11', 11" from sample tubes 12 of variable type 12', 12", and for reclosing the same tubes 12', 12" with the same respective closures 11', 11". The decapping/recapping device 100 can comprise six individual closure holders 20 arranged symmetrically on a rotatable carousel 61, having a respective number of arms 62, and each arm receiving one closure holder 20. Each closure holder can comprise a passive closure gripper 21 for holding a closure 11. The device 100 can further comprise three actuators 40 and, in particular, a decapping actuator 40' for actuating the passive closure grippers 21 when removing a closure 11 from a tube 12, a recapping actuator 40" for reclosing the tube 12 with its respective closure 11, and a waste actuator 40''' for eventually releasing a closure 11 into a waste compartment (not shown). The device 100 can further comprise two tube grippers 50. In particular, a fixed decapping station comprising a decapping tube gripper 50' aligned with the decapping actuator 40' and cooperating with the decapping actuator 40' for biasing a tube 12 and its closure 11 away from each other when removing the closure 11. A fixed recapping station comprising a recapping tube gripper 50" aligned with the recapping actuator 40" and cooperating with the recapping actuator 40" for biasing the tube 12 and its closure 11 towards each other when reclosing the tube 12. The decapping actuator 40' can be coupled to a passive closure gripper 21 of a closure holder 20 when a closure 11 is removed from a tube 12. The recapping actuator 40" can be coupled to a passive closure gripper 21 of a closure holder 20 when a tube 12 is reclosed with its respective closure 11. The waste actuator 40''' can be coupled to a passive closure gripper 21 of a closure holder 20 when a closure is disposed. An actuator 40 can be decoupled from a passive closure gripper 21 when the closure holder 20 is holding a closure 11.

The pipetting system 200 can further comprise a pipetting unit 150 synchronized with the decapping/recapping device 100 to withdraw a volume of sample from an opened sample tube or dispense a volume of liquid into the sample tube 12 in the time frame between the opening of a tube 12 and the reclosing of the tube 12 with the same closure 11.

Figures 2A, 2B:
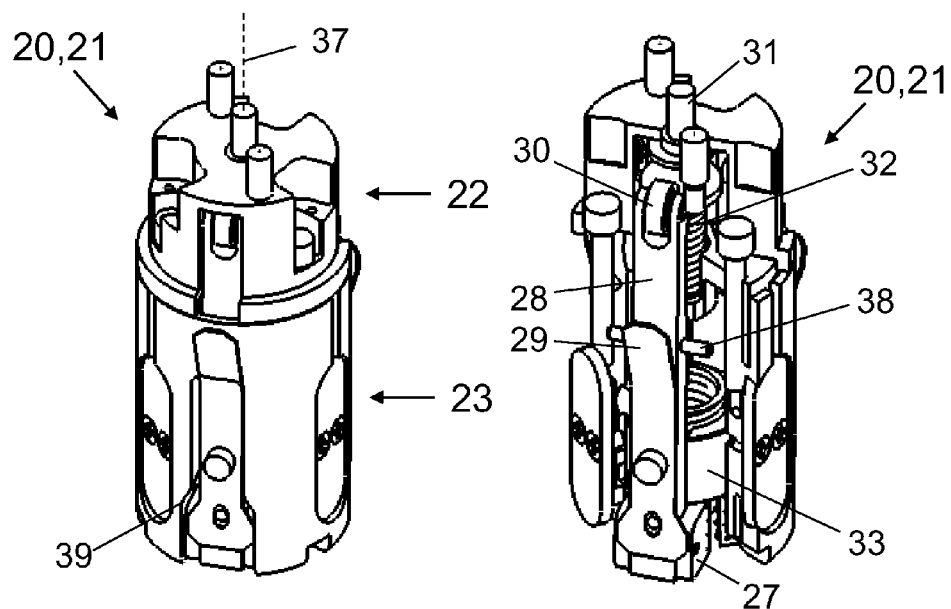
FIG. 2a illustrates one of the plurality of closure holders as illustrated in FIGS. 1a and 1b according to an embodiment of the present disclosure.
FIG. 2b illustrates the closure holder of FIG. 2a wherein part of the housing has been removed for making some of the inner components visible according to an embodiment of the present disclosure.
Figures 2C, 2D:
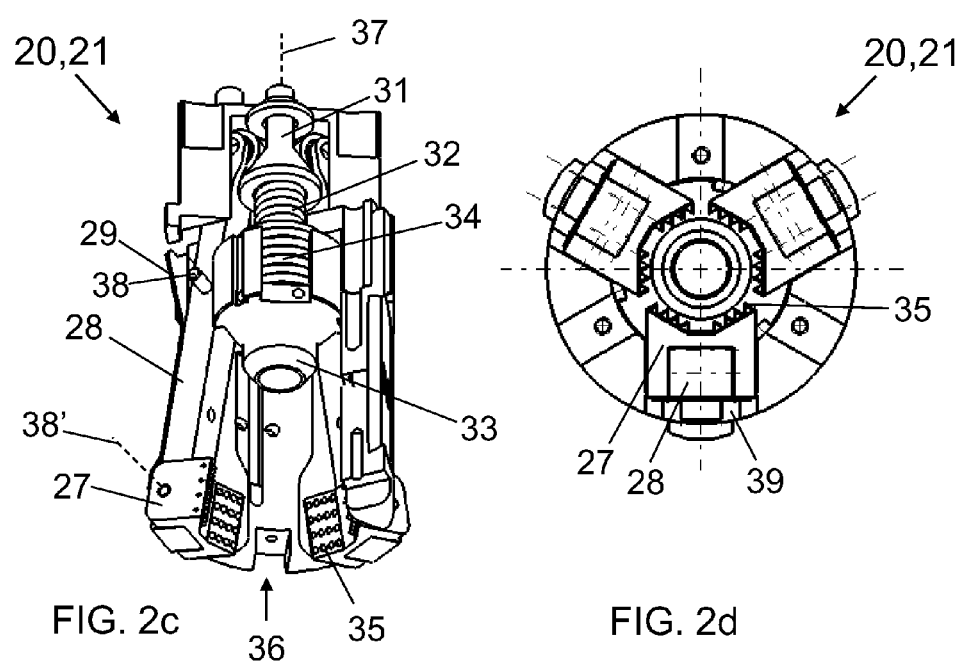
FIG. 2c provides further insight to the working principle of the closure holder of FIGS. 2a and 2b according to an embodiment of the present disclosure.
FIG. 2d illustrates a bottom view of the closure holder of FIG. 2a according to an embodiment of the present disclosure.

FIGS. 2a-d illustrate the structure of a closure holder 20 and the working mechanism of a passive closure gripper 21, according to one embodiment. In particular, FIG. 2a shows the closure holder 20 from outside. FIG. 2b shows the inside of the passive closure gripper 21 in its passive mode. FIG. 2c shows the inside of the passive closure gripper 21 when it is activated. FIG. 2d shows a bottom view of the closure holder 20 in its passive mode. The closure holder 20 can have a symmetrical construction comprising an upper coupling part 22 coupled to an actuator 40 and a lower cylindrical part 23 comprising a cavity 36 for receiving a closure 11 (closure not shown). The passive closure gripper 21 can comprise three cantilever arms 28 pivotable about horizontal fulcrum elements 38 and symmetrically arranged with respect to a central vertical axis 37 of the closure holder 20. Each cantilever arm 28 can comprise a jaw 27 mounted at the lower end and a wheel 30 mounted at the upper end. A cantilever spring 29 can be also mounted on one side of each cantilever arm 28 for exercising a force on the cantilever arm 28 such as the lower end and therefore the jaw 27 can be pushed towards the outside of the lower part 23 of the closure holder 20 in absence of other forces.

The passive closure gripper 21 can further comprise a pre-tensioning member comprising a passive element 31 and a coil spring 32 and symmetrical arranged with respect to the axis 37. The passive element 31 can comprise a pin protruding out of the coupling part 22 of the closure holder 20 along axis 37 and a lower conical part providing a surface of contact with the coil spring 32 at the bottom and with the wheels 30 on the side. The force applied by the coil spring 32 to the passive element 31 and therefore the force applied by the passive element 31 to the three cantilever arms 28 can be greater than the sum of the forces applied by the three cantilever springs 29 to the three cantilever arms 28. Thus, the force of the coil spring 32 prevails pushing the passive element 31 upwards and the wheeled ends of the cantilever arms outwards, i.e. the jawed ends of the cantilever arms 28 are pushed inwards against the force of the cantilever springs 29, which tend to push them outwards (FIG. 2b). Each jaw 27 can comprise two surfaces facing the inside of the closure holder 20, and forming an angle of substantially 120°. The three jaws 27 thus form a regular geometrical gripping surface (FIG. 2d) which enables a more efficient grip and prevents asymmetrical deformations of the closure 11. Further each jaw 27 can comprise a series of conical protrusions 35, which act as friction surface for an even better grip, i.e. for preventing sliding or misplacement during decapping, recapping or holding of the closure 11, while reducing the points of contact. If a closure 11 (not shown in FIG. 2a-2d) is located between the jaws 27, the pressure applied symmetrically to the outside of the closure 11 is such that the closure 11 can be held passively in place. In addition, each jaw 27 can pivot about a horizontal jaw axis 38' and can thus be capable of varying its angle relative to the central vertical axis 37 of the closure holder. This can enable the jaws to adapt to different inclinations of the sides of a closure 11 without losing gripping surface and power.

Upon coupling with an actuator 40 (not shown in FIG. 2a-2d), a force can externally be applied to the passive element 31, which can be greater than the force of the coil spring 32. The passive element 31 can therefore be pushed downwards allowing the wheeled part of the cantilever arms 28 to disengage. The only force acting on the cantilever arms 28 is at this point that of the cantilever springs 29, which thus push the jawed ends of the cantilever arms 28 outwards (FIG. 2c), hence opening the jaws 27 and releasing the pressure from a closure 11 in between or allowing a new closure 11 to be inserted between the open jaws 27 before they are closed again. The lower part 23 of the closure holder 20 can comprise an aperture 39 in correspondence to each cantilever arm 28 through which the jawed end of the cantilever arm 28 can extend when opening or when accommodating a closure 11 of larger diameter.

The closure holder 20 can further comprise a passive closure push element 33 comprising a resilient member, i.e. a second coil spring 34, for exercising a push force on the closure 11 in a vertical direction when the passive pressure of the jaws 27 is released. The push element 33 is shown in its relaxed position in FIG. 2b and in its tensioned position in FIG. 2c. The resilient force of the resilient member can be chosen such that it is weaker than the resilient force of the pre-tensioning member. In this way, upon inserting a closure 11 between the gripping tool, i.e. by lifting a closed sample tube 12 towards the closure holder 20, the push element 33 can be pushed upwards by the closure 11 and the second coil spring 34 can be tensioned. Therefore, as long as the closure 11 remains tight between the jaws 27, during the holding period, the push element 33 is limited to exercise only a pressure on the top of the closure 11. In the event that the closure 11 has to be disposed, the push element 33 can provide a push impulse to the closure 11 contributing to expel it downwards out of the closure holder 20 when opening the jaws 27. The push element 33 is further fit with its bottom into a concave top of certain types of closure 11', such as to prevent asymmetrical deformation and/or tilting of the closure 11' when the jaws 27 apply a pressure on its sides, thus acting as a stabilizer of the closure 11'.

Figure 3:
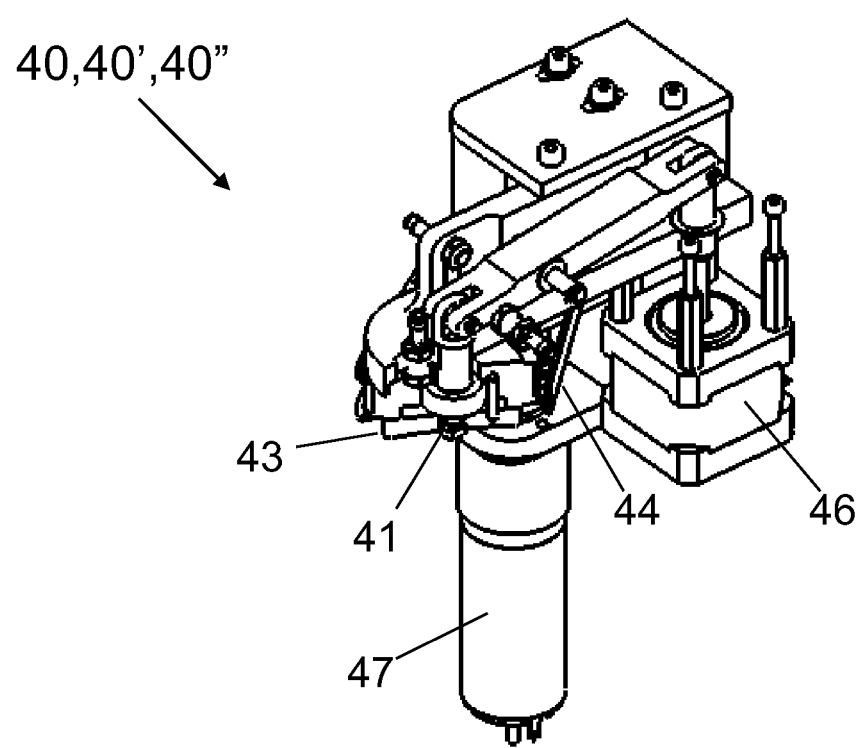
FIG. 3 illustrates an actuator with some parts removed to reveal some inner components according to an embodiment of the present disclosure.

FIG. 3 shows an actuator 40, such as the decapping actuator 40' and the recapping actuator 40" wherein some parts are removed for illustrative purpose. The actuator 40, 40', 40" can comprise an active bolt 41 connected to a spindle motor 46 for exercising a pressure on the passive element 31 of a passive closure gripper 21 when the actuator 40, 40', 40" and the passive closure gripper 21 are in coupling connection, the force applied by the active bolt 41 can be greater than the force of the first coil spring 32. Thus, the active bolt 41 acting on the passive element 31 can have the function to indirectly open the jaws 27, every time a closure 11 needs to be gripped or released. The actuator 40, 40', 40" can further comprise a closure-gripper drive comprising a coupling disc 43 connected to a DC stepper motor 47 via drive belt 44 for rotating the closure holder 20 about its axis 37. The engagement between coupling disc 43 and coupling part 23 of the closure device 20 is discussed below with reference to FIGS. 6a to 6c.

In case of the waste actuator 40''' (shown in FIG. 1b), there is normally no need for rotating the passive closure gripper 21 but only to release the pressure applied to the closure 11 by opening the jaws 27. Therefore the waste actuator 40''' can comprise the active bolt 41 but no closure-gripper drive for rotating the passive closure gripper 21.

Figure 4A:
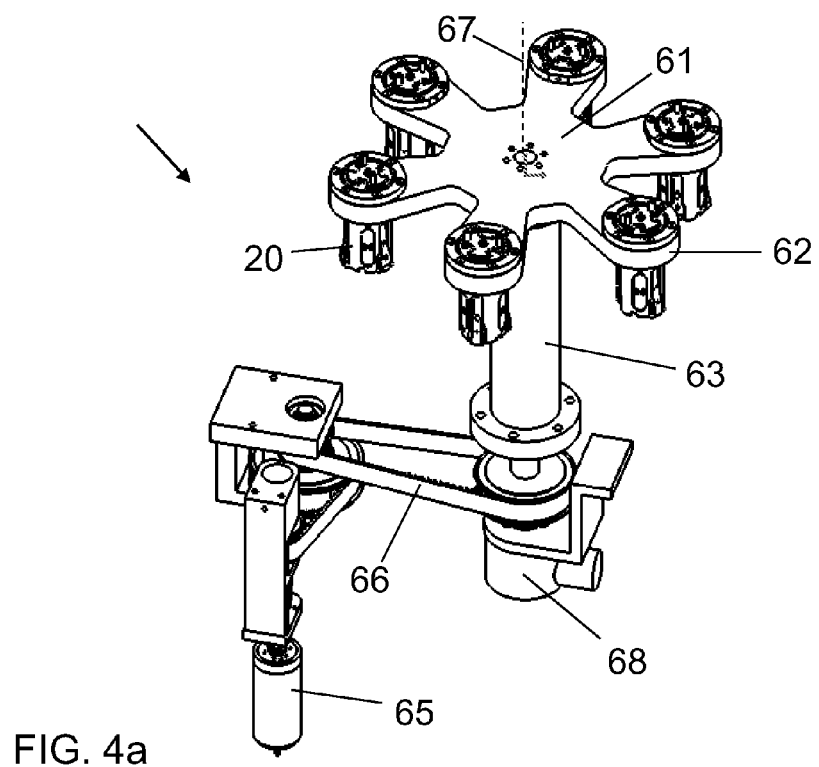
FIG. 4a illustrates a carousel-like rotor carrying a plurality of closure holders as illustrated in FIGS. 1a and 1b according to an embodiment of the present disclosure.
Figure 4B:
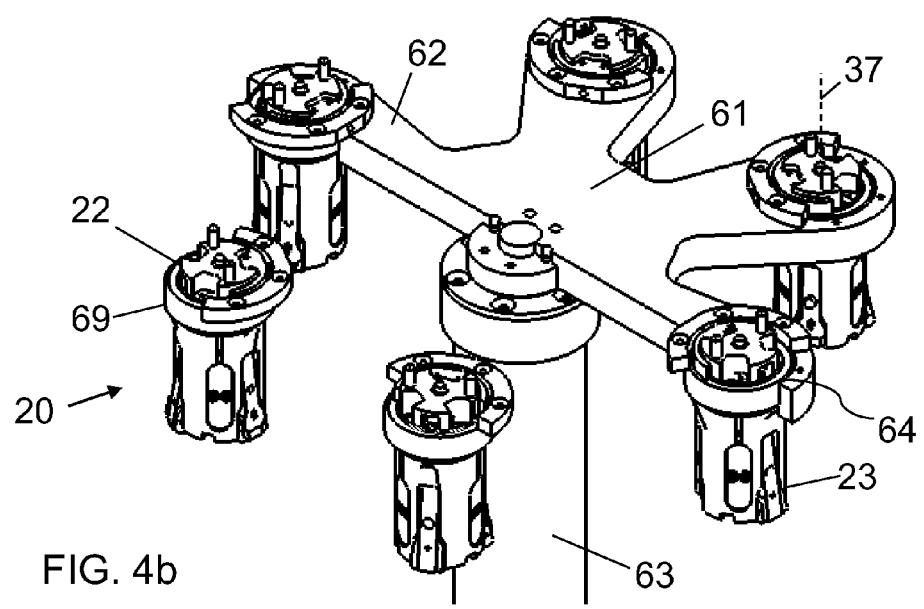
FIG. 4b illustrates a partially cut view of the carousel of FIG. 4a according to an embodiment of the present disclosure.

FIGS. 4a and 4b refer to closure-holder drive 60. The closure-holder drive 60 can comprise a carousel 61 comprising six arms 62, each carrying one of the six closure holders 20 as illustrated in FIGS. 1a and 1b. The carousel 61 can be mounted on a rotor 63 connected to a DC stepper motor 65 via a belt 66 for being rotated about an axis 67 in order to bring sequentially the closure holders 20 in coupling connection with any of the actuators 40. The closure-holder drive 60 can further comprise a position sensor 68 assisting in determining the initial correct position and for controlling/monitoring the angle of rotation such as to facilitate a proper alignment between actuators 40 and closure holders 20 at every rotation.

FIG. 4b is a partially cut view of the carousel 61 of FIG. 4a showing how a closure holder 20 can be mounted on an arm 62 of the carousel 61. In particular, a disc 69 can be concentrically fixed around the coupling part 22 of the closure holder 20. The disc 69 can then be sandwiched into a chamber 64 of the arm 62 such as the lower part 23 of the closure holder 20 extends below the arm 62, the coupling part 22 of the closure holder 20 extends in part above the arm 62 and the whole closure holder 20 comprising the disc 69 is rotatable about the axis 37 with respect to the chamber 64.

Figure 5:
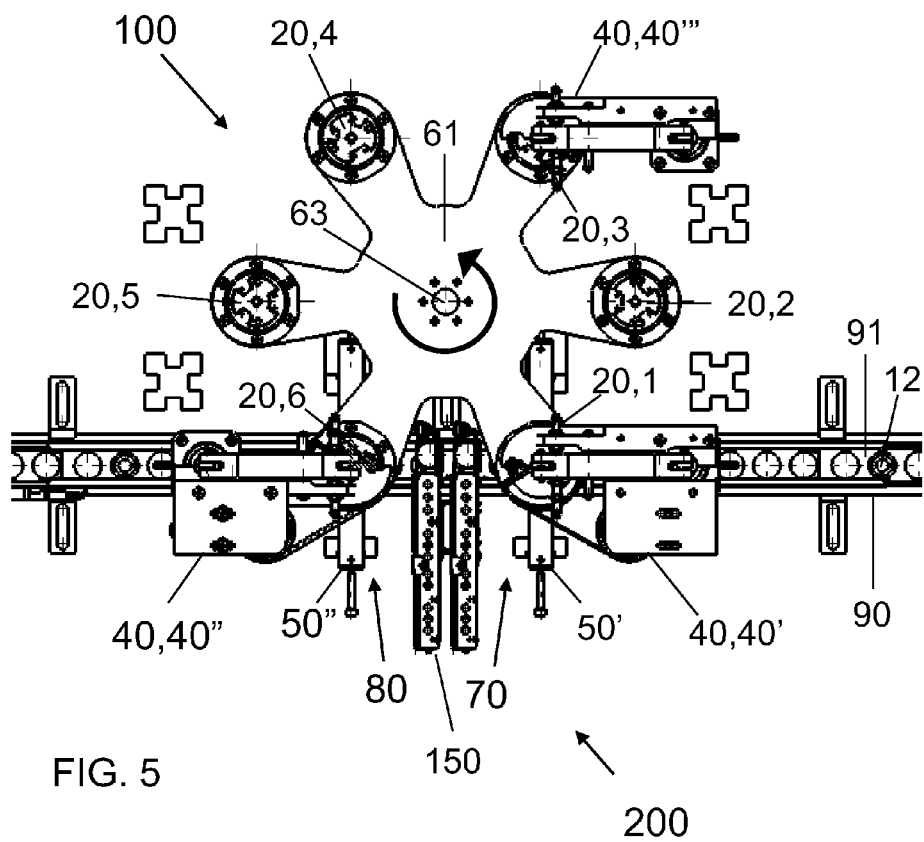
FIG. 5 illustrates a top view of the system of FIG. 1a wherein some parts have been removed for clarity according to an embodiment of the present disclosure.

FIG. 5 is a top view of the system 200 of FIG. 1a wherein some parts have been removed for clarity. The actuators 40 can be fixed while the carousel 61 is rotatable counterclockwise. Six closure holders 20 numbered respectively 1 to 6 can be arranged symmetrically at intervals of approximately 60° and at a distance from the center of the rotor 63, which can correspond to the distance of the active bolts 41 of the actuators 40 measured from the center of the rotor 63. The actuators 40 can also be arranged with respect to each other so that coupling between a passive closure gripper 21 and any actuator 40 is possible upon rotating the rotor 63 of regular steps, in this case 60° or multiples of 60°. The device 100 can further comprise a tube conveyor, in this case, a linear conveyor 90 to transport tube racks 91, each carrying up to 5 sample tubes 12. The distance between the decapping actuator 40' and the recapping actuator 40" can correspond to the distance between the centers of six tubes 12, i.e. between two tubes 12 occupying the same respective position on two adjacent racks 91. In this way, two tubes 12 may be brought in alignment with two closure holders 20 and two actuators 40 at the same time. The conveyor 90 can be being synchronized with the rotor 63 to advance the racks 91 stepwise such as a new tube 12 and a new closure holder 20 are brought in alignment at the same time with the same actuator 40, in this case either the decapping actuator 40' or the recapping actuator 40". The decapping tube gripper 50' and the recapping tube gripper 50" are also aligned with the decapping actuator 40' and recapping actuator 40" respectively. The decapping tube gripper 50' can be synchronized with the conveyor 90 to lift a tube 12 and with the rotor 63 to bring a free closure holder 20 in coupling connection with the decapping actuator 40' such as to remove a closure 11 from that tube 12 at that position at that time. The recapping tube gripper 50" can be synchronized with the conveyor 90 to lift a tube 12 and with the rotor 63 to bring the same closure holder 20 holding the closure 11 previously removed from that same tune 12 in coupling connection with the recapping actuator 40" such as to reclose that tube 12 at that position at that time.

One possible workflow of the decapping/recapping device 100 according to this embodiment is summarized in the following example. At start, all six closure holders 20 can be free. The device 100 can be initialized, via position sensor 68 (not shown in FIG. 5), such as a closure holder 20, e.g. closure holder 20, 1 is aligned with the decapping actuator 40'. The conveyor 90 can then be instructed to advance the racks 91 such that as the first tube 12 on the first rack 91 is brought in alignment with the decapping actuator 40' and therefore with the closure holder 20, 1 and the decapping tube gripper 50'. The dacapping actuator 40' is coupled to the passive closure gripper 21 of closure holder 20,1 such that as the active bolt 41 applies a force on passive element 31 thereby causing the jaws 27 to be opened. The decapping tube gripper 50' is instructed to lift the tube 12 until the closure 11 is at a height between the open jaws 27. In order to determine the height, account is taken of a measurement carried out by a sensor (not shown) during the advancement of the rack 91 determining the type of tube 12 and/or closure 11. The jaws 27 are then closed by releasing the pressure by the active bolt 41. The decapping actuator 40' is then instructed to rotate the coupling disc 53 for rotating the passive closure gripper 21, while the decapping tube gripper 50' is instructed to pull the tube 12 downwards back on the rack, thereby cooperating with the decapping actuator 40' to remove the closure 11 from the tube 12 via passive closure gripper 21 of closure holder 20, 1.

The rack 91 can then be advanced to another position, such as the next tube 12 is brought into alignment with the decapping actuator 40' and the decapping tube gripper 50'. At the same time, the next closure holder 20, 6 is brought in alignment with the decapping actuator 40' by rotating the rotor 63 of 60° counterclockwise and the procedure is repeated. The closure holder 20, 1 has thus moved to 60° counterclockwise while holding passively the closure 11 removed from the first tube 12, the closure holder 20, 1 no longer being coupled to any actuator 40.

Performing this step five times, five tubes 12 have been opened and respective closures have been transported stepwise counterclockwise 60° at a time by respective passive closure holders 20, 1, 2, 3, 4, 5. When closure holder 20, 6 comes into alignment with decapping actuator 40', closure holder 20, 1 holding the first closure 11, comes into alignment with recapping actuator 40". At the same time, while the 6$^{th}$ tube 12, i.e. the first tube on the second rack 91, comes in alignment with the decapping tube gripper 50' and decapping actuator 40', the first tube 12 on the first rack 91, which was first opened, comes into alignment with the recapping tube gripper 50" and recapping actuator 40", therefore with closure holder 20, 1 holding its respective closure 11, i.e. the same closure 11 removed from that same tube 12.

From this point on, the decapping station 70 and recapping station 80 will work in the same time frame, each performing its respective task of decapping and recapping. In particular, nearly the same steps of those carried out at the decapping station 70 occur at the recapping station 80 but in reverse order. Specifically, at the recapping station 80, the recapping actuator 40" is instructed to rotate the coupling disc 43 for rotating the passive closure gripper 21 in the opposite direction, while the recapping tube gripper 50' is instructed to lift the tube 12 upwards towards the closure 11, using the same information on the type of tube already acquired, thereby cooperating with the decapping actuator 40' to reclose the tube 12 with the same closure 11 via passive closure gripper 21 of closure holder 20,1. It is to be noted that the angular position of the closure 11 with respect to the tube 12 is different at the decapping station 70 and the recapping station 80 respectively. This is due to the fact that the tube 12 has been transported linearly from the dacapping station 70 to the recapping station 80 without rotating on itself. On the other hand, the closure holder 20,1 has been transported with a rotational movement of the rotor 63 of 300° counterclockwise from the decapping station 70 to the recapping station 80. There is therefore a difference of −60° in the angular position of the closure 11 with respect to the tube 12 at the recapping station 80 compared to the decapping station 70. This difference may have an influence on the proper closing of a tube 12, especially if the closure 11 is of the screw type. In order to take account of this difference, the recapping actuator 40" is instructed to rotate the coupling disc 43 for rotating the passive closure gripper 21 of an additional 60°. The active bolt 41 applies then a force on passive element 31 thereby causing the jaws 27 to be opened and the recapping tube gripper 50" is instructed to lower the tube 12 on the rack 91. The recapping actuator 40" is thus decoupled from the closure holder 20, 1, which is again free to return to the decapping station 70 for receiving a new closure and starting a new cycle.

The pipetting unit 150 can be synchronized with the decapping/recapping device 100 to withdraw a volume of sample and/or dispense a volume of liquid in the time frame between the opening of a tube 12 and the reclosing of the tube 12 with the same closure 11. In particular, the pipetting unit 150 can be temporarily lowered such as a needle (not shown in FIG. 5) is dipped into a sample via the open end of a tube 12 when the tube 12 is at an intermediate position between the decapping station 70 and the recapping station 80 and during the time frame in which the decapping station 70 and/or the recapping station 80 are operating with other respective tubes and the rotor 63 is not rotating. Optionally a pipetting tube gripper (not shown) may be employed to lift the open tube 12 and facilitate the pipetting operation by shortening the distance of travel of the pipetting unit 150.

Figure 6A:
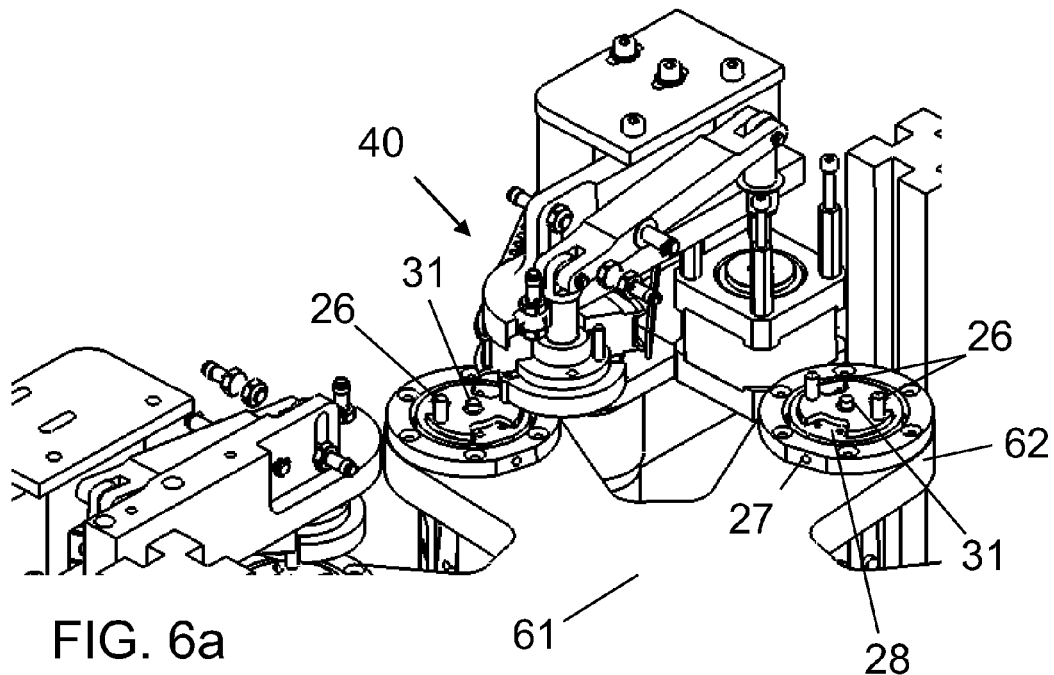
FIGS. 6a-b illustrate in perspective from top and bottom respectively how an actuator and a passive closure gripper are being engaged (some parts removed for clarity) according to an embodiment of the present disclosure.
Figure 6B:
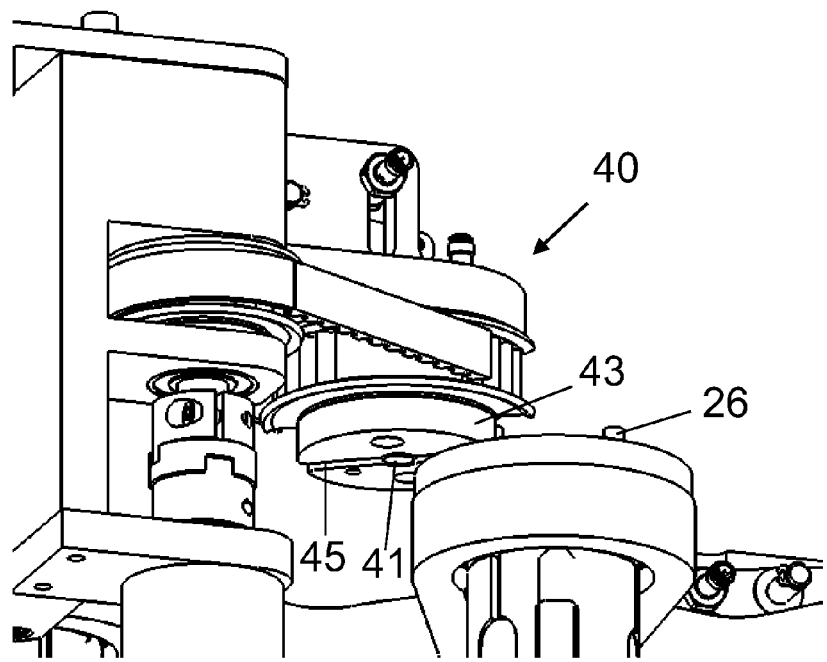

FIGS. 6a and 6b show in perspective from top and bottom respectively how an actuator 40, in particular a decapping actuator 40' and recapping actuator 40" can be engaged with a passive closure gripper 21 (some parts removed for clarity). In particular, the coupling part 23 of the closure holder 20 can comprise two pins 26 on its upper surface located on opposite sides of the passive element 31 located at the center. The passive element 31 can lay out of the line between the two pins 26 so that when the closure holder 20 is mounted on an arm 62 of the carousel 61, the passive element 31 and the two pins 26 can lay on a an imaginary circle having as radius the distance between the center of the passive element 31 and the center of the rotor 63. The coupling disc 43 can comprise on the bottom a groove 45 having a width and a depth large enough to allow the pins 26 and the passive element 31 to fit in. Additional the groove 45 can have a curvature corresponding to that of an imaginary circle having as radius the distance between the center of the active bolt 41 and the center of the rotor 63 such as the pins 26 and the passive element 31 can pass smoothly through when the carousel 61 is rotated. Engagement can be complete when the passive element 31 and the active bolt 41 are in alignment. The active bolt 41 can be extendable and retractable through a hole in the center of the groove 45.

Each arm 62 can comprise alignment device, such as a magnet 27 to attract a ferromagnetic element 28 located on one side of the coupling part 23 of each closure holder 20.

Each magnet 27 and each ferromagnetic element 28 can be located such that when the closure holder 20 is decoupled from an actuator 40, due to the magnetic force exercised by the magnet 27 on the ferromagnetic element 28, rotation of the closure element 20 about its axis 37 is prevented and the same angular position of the closure holder 20 with respect to its respective arm 62 is maintained during rotation of the rotor 63. Each magnet 27 and each ferromagnetic element 28 can be located such that the pins 26 of the closure holder 20 are aligned with groove 45 when a closure holder 20 is be coupled to an actuator 40. When the closure holder 20 is coupled to a decapping actuator 40' or recapping actuator 40" the coupling disc 43 can apply a rotational force to the closure holder 20 via groove 45 acting on the pins 26, which can be greater than the magnetic force, thereby causing rotation of the closure holder 20 about its axis 37.

Figure 6C:
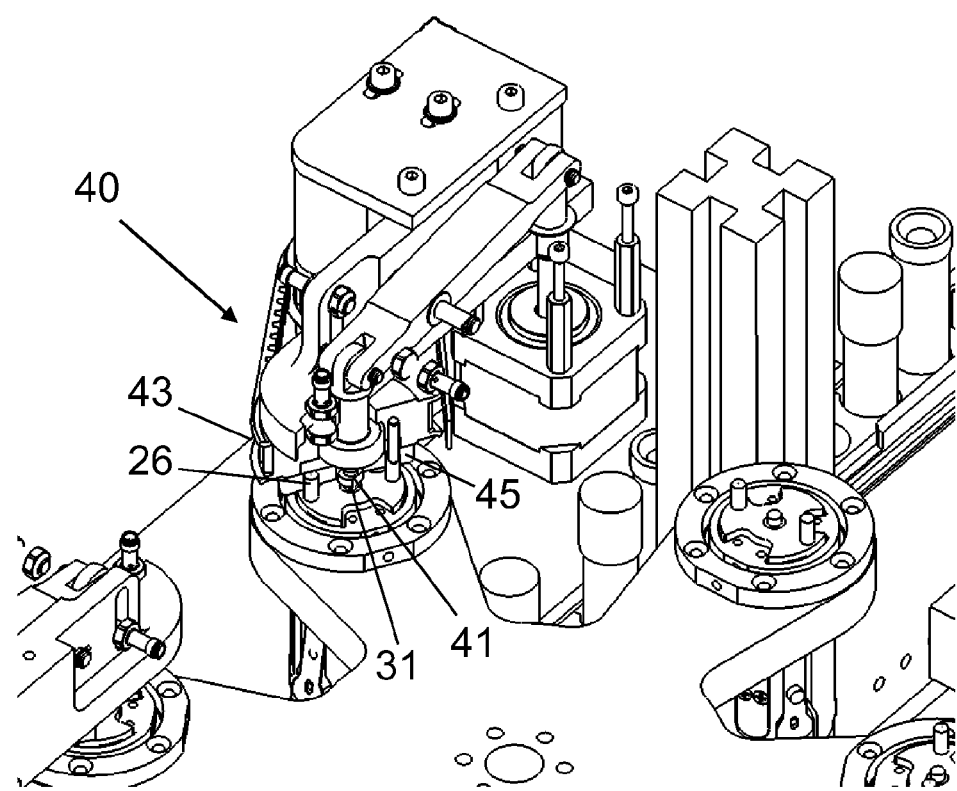
FIG. 6c illustrates the actuator and passive closure gripper of FIGS. 6a and 6b already engaged (some parts removed for clarity) according to an embodiment of the present disclosure.

FIG. 6c shows the actuator 40 and passive closure gripper 21 already engaged (some parts removed for clarity). The pins 26 and passive element 31 can be inside the grove 45. The active bolt 41 can be aligned with the passive element 31. In addition, the active bolt 41 is shown while applying a force to the passive element 31 thereby establishing a first coupling connection between the actuator 40 and the passive closure gripper 21. Upon rotation of the coupling disc 43, a rotational force can also be applied to the closure holder 20, thereby establishing a second coupling connection. A coupling connection can occur at the time when a force is transferred from the actuator 40 to the closure holder 20 or passive closure gripper 21. A closure holder 20 may be engaged, i.e. aligned with an actuator 40 without coupling taking place if not necessary. This is the case for example with the waste actuator 40'''. Moreover, engagement with the waste actuator 40''' can comprise only alignment between the active bolt 41 and passive element 31. Also, coupling can comprise only a transfer of force from the active bolt 41 to the passive element 31.

Figure 7:
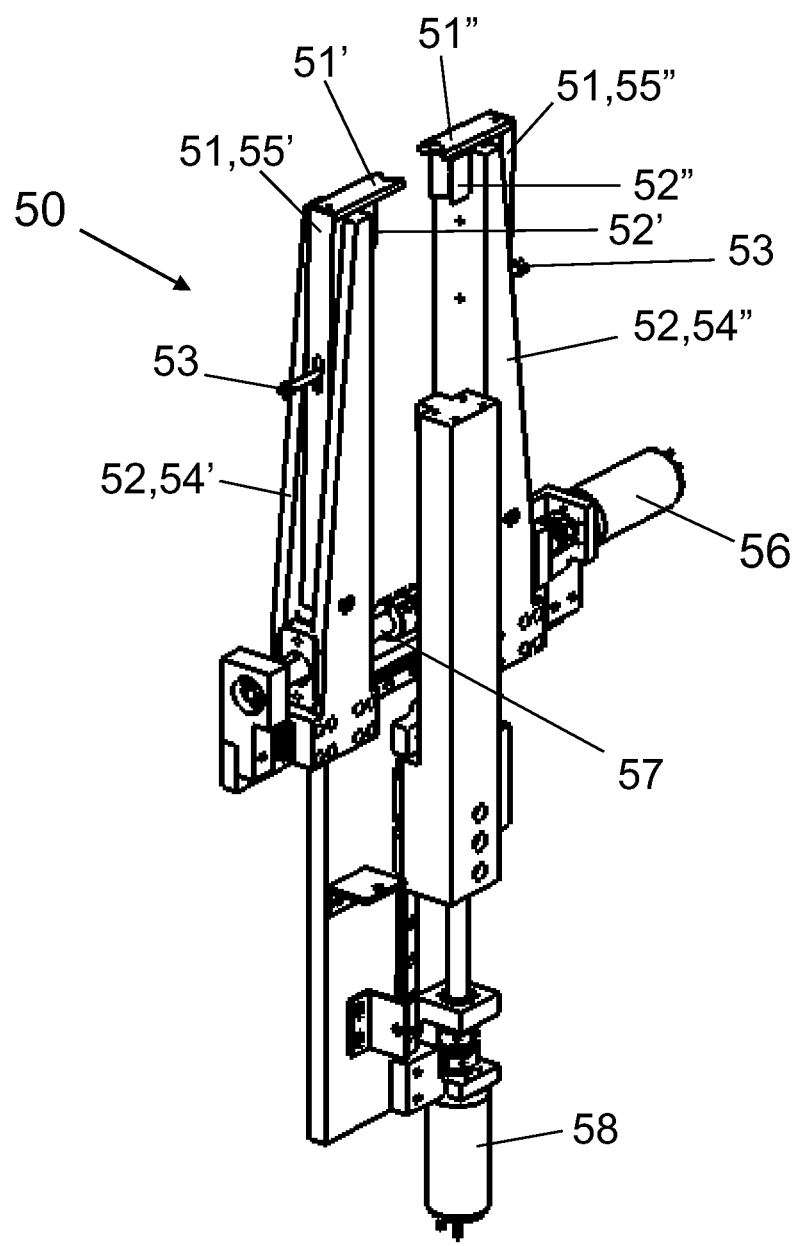
FIG. 7 illustrates a tube gripper in more detail according to an embodiment of the present disclosure.

FIG. 7 shows a tube gripper 50 in detail. The tube gripper 50 can comprise a first tube gripping tool 51 comprising two upper tube gripping jaws 51', 51" mounted on two respective first tube gripping arms 55' and 55", biasable with respect to each other. The tube gripper 50 can further comprise a second tube gripping tool 52 comprising two lower tube gripper jaws 52' and 52" mounted on two respective second tube gripping arms 54' and 54", biasable with respect to each other and in the same direction as the upper tube gripping jaws 51', 51". In addition, first tube gripping arms 55' and 55" can be mounted on second tube gripping arms 54' and 54" respectively and are biasable with respect to second tube gripping arms 54' and 54" via a resilient device 53. Upper tube gripping jaws 51', 51" and lower tube gripping jaws 52' and 52" each can comprise a gripping surface for gripping a tube from opposite sides respectively, wherein the upper tube gripping jaws 51', 51" are longer than the lower tube gripping jaws 52' and 52" and the gripping surface of the upper tube gripping jaws 51', 51" can be smaller that the gripping surface of the lower tube gripping jaws 52' and 52". The tube gripper 50 can further comprise a first DC stepper motor 56 connected via spindle drive 57 to second tube gripping arms 54' and 54" for biasing the second gripping arms 54' and 54" and therefore lower tube gripping jaws 52' and 52" towards each other when gripping a tube 12 and away from each other when releasing a tube 12. Since first tube gripping arms 55' and 55" are mounted on second tube gripping arms 54' and 54", they can also be biased accordingly. The tube gripper 50 can further comprise a second DC stepper motor 58 for lifting and lowering second tube gripping arms 54' and 54" and together first tube gripping arms 55' and 55". Since upper tube gripping jaws 51' and 51" are longer than lower tube gripping jaws 52' and 52" and biasable with respect to each other via resilient means 53, the tube gripper 50 may be set up via motors 56 and 58 such that the upper tube gripping jaws 51' and 51" can grip and lift a tube from a tube carrier before the lower tube gripping jaws 52' and 52" can grip and hold securely a tube with a force and a surface of contact which can be greater than the force and surface of contact of the upper tube gripping jaws 51', 51" respectively. Analogously, the tube gripper 50 may be set up such that the lower tube gripping jaws 52' and 52" can release the tube before the upper tube gripping jaws 51' and 51" when lowering the tube back on the tube carrier.

Figure 8A:
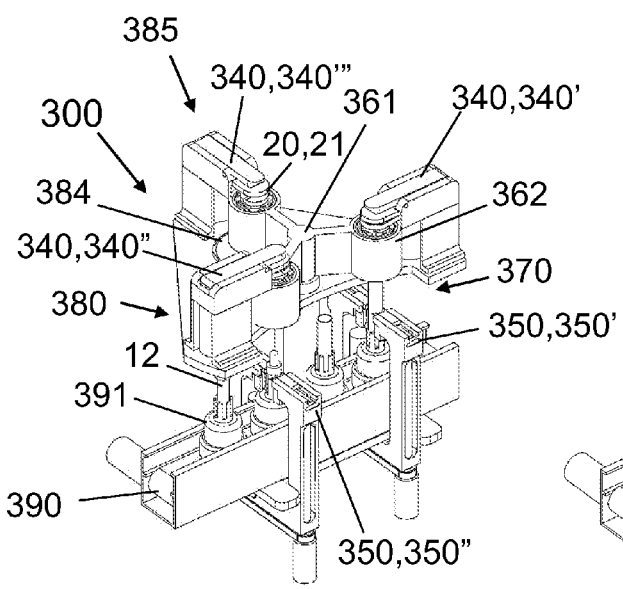
FIG. 8a illustrates a perspective view of a decapping/recapping device according to another embodiment of the present disclosure.

FIG. 8a shows a perspective view of a decapping/recapping device 300 according to another embodiment. The difference with the decapping/recapping device 100 of FIG. 1b and FIG. 5 is that it operates with single tube carriers 391 transported by conveyor 390. In particular, the decapping/recapping device 300 can comprise a fixed decapping actuator 340' and a decapping tube gripper 350, 350' aligned at a decapping station 370, a recapping actuator 340" and a recapping tube gripper 350, 350" aligned at a recapping station 380, a waste actuator 340''' and a waste well 384 aligned with a waste compartment (not shown) at a waste station 385. Three closure holders 20 can be arranged symmetrically at intervals of about 120° on three respective arms 362 of a carousel 361, which can rotate counterclockwise via rotor 363. The decapping station 370, the recapping station 380 and the waste station 385 can also be arranged with respect to each other so that coupling between a passive closure gripper 21 and any actuator 340 is possible upon rotating the rotor 363 of regular steps of about 120° or multiples of about 120°. The device 300 can further comprise a tube conveyor, in this case a linear conveyor 390 to transport pucks 391, each carrying a single tube 12. The distance between the decapping station 370 and the recapping station 380 can correspond to the distance between the centers of a first and third tube in a series of three tubes 12 carried by respective pucks 391 adjacent to each other. In this way, two tubes 12 may be brought in alignment with two closure holders 20 and two actuators 340', 340" at the same time. The workflow of this embodiment may be analogous to that described with reference to FIG. 5, except that a cycle can be completed every three tubes instead of six and the steps of rotation are of 120° instead of 60°.

Figure 8B:
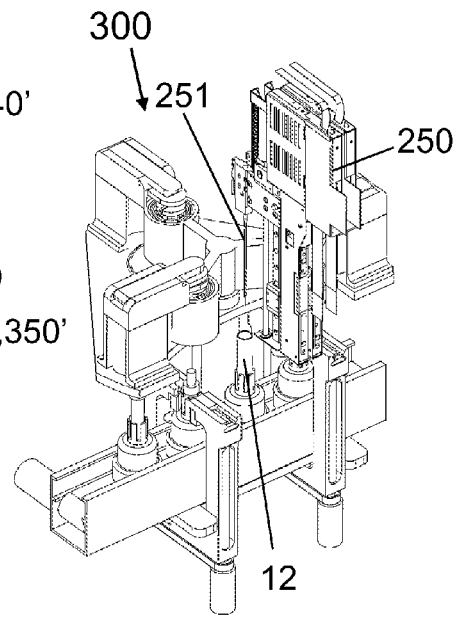
FIG. 8b illustrates a pipetting system comprising the decapping/recapping device of FIG. 8a according to an embodiment of the present disclosure.

FIG. 8b shows a pipetting system 400 comprising the decapping/recapping device 300 of FIG. 8a. The pipetting system 400 can further comprise a pipetting unit 250 synchronized with the decapping/recapping device 300 to withdraw a volume of sample and/or dispense a volume of liquid in the time frame between the opening of a tube 12 and the reclosing of the tube 12 with the same closure 11. In particular, the pipetting unit 250 can be temporarily lowered so that a needle 251 can be dipped into a sample via the open end of a tube 12 when the tube 12 is at an intermediate position between the decapping station 370 and the recapping station 380 and during the time frame in which the decapping station 370 and/or the recapping station 380 are operating with other respective tubes and the rotor 63 is not rotating. Optionally a pipetting tube gripper (not shown) may be employed to lift the open tube 12 and facilitate the pipetting operation by shortening the distance of travel of the pipetting unit 250 and/or of the pipetting needle 251.

Figure 8C:
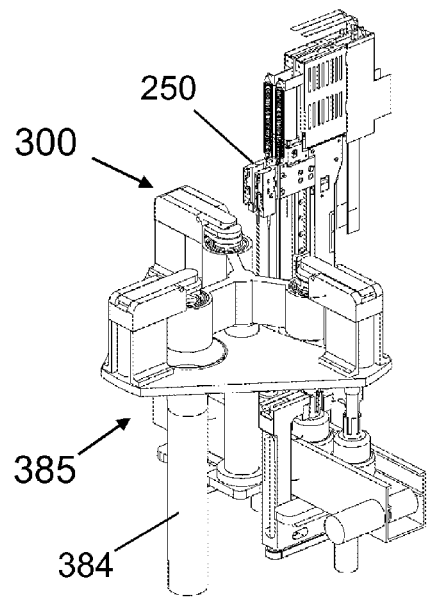
FIG. 8c illustrates the pipetting system of FIG. 8b from another perspective according to an embodiment of the present disclosure.

FIG. 8c shows the same pipetting system 400 of FIG. 8b from another perspective. In particular the waste station 385 is more clearly shown, comprising a waste well 384 for guiding closures to be disposed into a waste compartment (not shown).

Figure 8D:
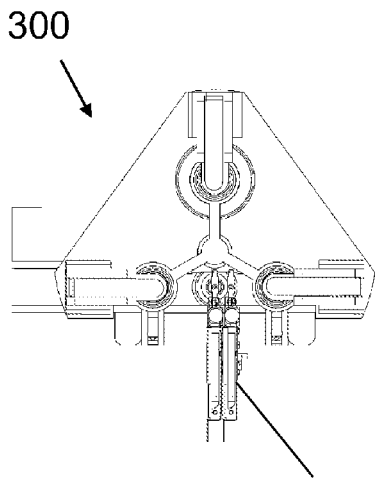
FIG. 8d illustrates a top view of the same pipetting system of FIGS. 8b and 8c according to an embodiment of the present disclosure.

FIG. 8d shows a top view of the same pipetting system 400 of FIGS. 8b and 8c for better appreciating the difference with FIG. 5.

Figure 9:
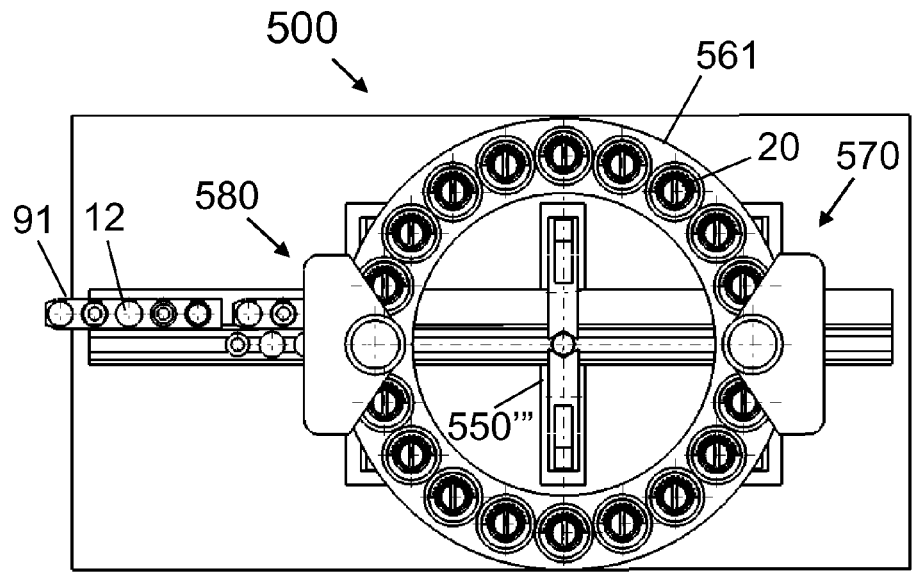
FIG. 9 illustrates a top view of a decapping/recapping device according to another embodiment of the present disclosure.

FIG. 9 shows more schematically a top view of a decapping/recapping device 500 according to another embodiment, in operation with tube racks 91. The difference with the previous embodiments is that carousel 561 can have the shape of a ring and can accommodate a larger number of closure holders 20, in this case twenty. Further, only a decapping station 570 and recapping station 580 are shown, which can be arranged diametrically opposite with respect to the carousel 561. A cycle is in this case can complete every eleven tubes 12. It can be also noted that a pipetting tube gripper 550''' can be arranged at the center of the device 500 to lift one of the opened tubes 12 when the tube 12 passes at that position and to facilitate the pipetting operation by shortening the distance of travel of the pipetting unit (not shown).

Figure 10:
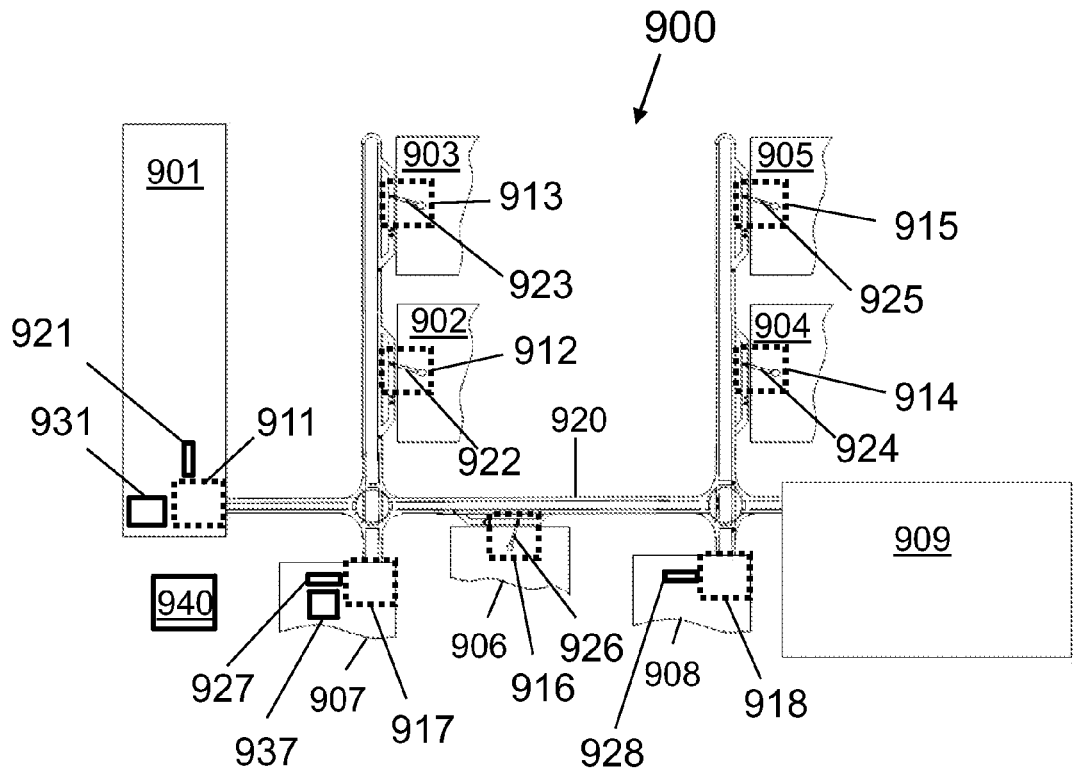
FIG. 10 illustrates schematically a system for processing sample tubes comprising a plurality of work cells and a plurality of pipetting systems according to an embodiment of the present disclosure.

FIG. 10 shows schematically only one example of a system 900 for processing sample tubes. The system 900 can comprise a plurality of work cells 901-909. In particular, the system 900 can comprise a pre-analytical work cell 901, a post-analytical work-cell 909, a plurality of analytical work-cells 902-906 to process sample tubes on single carriers and two analytical work-cells 907,908 to process sample tubes on tube racks. The system 900 can further comprise a transportation unit 920 to transport sample tubes on both single carriers and tube racks from one work cell to any other work cell according to the need. The system 900 can further comprise a pipetting system 911-918 in correspondence to each work cell 901-908 respectively, for withdrawing a volume of sample from a sample tube to be processed by the work cell 901-908. The pipetting system 911-918 can comprise a decapping/recapping device for removing a closure from a sample tube when a sample needs to be withdrawn and for reclosing the sample tube before it is transported by the transportation unit 920 to another work cell 901-909.

A decapping or decapping and recapping device can comprise a plurality of individual passive closure holders each comprising a passive closure gripper, and at least one actuator for actuating the passive closure gripper when removing a closure or reclosing a tube. One actuator can be coupled to one passive closure gripper when a closure has to be removed from a tube or when a closure has to be released from the closure gripper and can be decoupled from a passive closure gripper when the closure holder is holding a closure. This can increase processing throughput without the need to use additional closures and without severe limitations on processing steps. In this way also cost savings can be obtained by avoiding the use of additional closures and by a reduced complexity of the device.

Another advantage can be that the device enables to process sample tubes of variable shape and with closures of variable shape. This can enable the processing of primary tubes as well as secondary tubes.

Another advantage can be the risk of cross-contamination can be minimized.

Another advantage can be the throughput can also be increased even if the device is used as a decapping device only.

Another advantage can be that sample processing throughput in a system comprising a plurality of work-cells can be optimized. This can be achieved by having a decapping/recapping device for each work cell for removing a closure from a primary tube when and where a sample needs to be withdrawn and for reclosing the primary tube before it is transported to another work cell.

An advantage can be that tubes may be transported closed by a closure within the system, that is from one work-cell to another and opened only when and where needed. In this way the risk of spilling samples out of the tubes, the risk of cross-contamination, evaporation and the bio-hazard risk can be minimized.

Using a decapping/recapping device can enable the adaptation of the throughput of decapping and recapping of sample tubes to the sample processing throughput and the specific workflow of each work cell without depending by the throughput of a central or common decapping/recapping device. It can also be possible to adapt the decapping/recapping device to the type of sample tube carrier required by each work cell, which may differ from one another, e.g. single tube carrier or rack for carrying a plurality of sample tubes.

It should be clear that the above are just examples of some embodiments and that variations are possible according to the particular need without departing from the scope of the disclosure. In particular, a decapping/recapping device may be designed to operate with both single tube carriers and tube racks, wherein tube racks may carry a different number of tubes. Also, a different combination of the number of closure holders and actuators as well as a different arrangement may be conceived. Especially, a different coupling mechanism may be conceived.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A decapping device for removing closures from sample tubes, the decapping device comprising:
   a plurality of individual closure holders, each individual closure holder comprising a passive closure gripper for holding a closure;
   at least one actuator for actuating the passive closure gripper when removing a closure from a tube or releasing a closure, wherein the at least one actuator is coupled to the passive closure gripper of an individual closure holder when removing a closure from a tube or when releasing a closure and is decoupled from the passive closure gripper when the individual closure holder is holding a closure; and
   at least one tube gripper cooperating with the at least one actuator for biasing a tube and its closure away from each other when removing the closure.

2. The decapping device according to claim 1, wherein the passive closure gripper comprises a plurality of jaws, wherein the plurality of jaws comprise protrusions and cooperate with each other to grip and hold a closure.

3. The decapping device according to claim 2, wherein each jaw is pivotable about a horizontal jaw axis by varying its angle relative to the central vertical axis of the closure holder such as to adapt to different inclinations of the sides of the closure.

4. A decapping/recapping device for removing closures from sample tubes and for reclosing the sample tubes with the same respective closures, the decapping/recapping device comprising:
   a plurality of individual closure holders, each individual closure comprising a passive closure gripper for holding a closure;

at least one actuator for actuating the passive closure gripper when removing a closure from a tube or reclosing a tube with its respective closure, wherein the at least one actuator is coupled to the passive closure gripper of an individual closure holder when removing a closure from a tube or when reclosing a tube with its respective closure and is decoupled from the passive closure gripper when the individual closure holder is holding a closure; and at least one tube gripper cooperating with the at least one actuator for biasing a tube and its closure away from each other when removing the closure and for biasing the tube and its closure towards each other when reclosing the tube.

5. The decapping/recapping device according to claim 4, wherein the passive closure gripper comprises a plurality of jaws.

6. The decapping/recapping device according to claim 5, wherein the plurality of jaws comprise protrusions and cooperate with each other to grip and hold a closure.

7. The decapping/recapping device according to claim 4, wherein the closure holder comprises a passive closure push element.

8. The decapping/recapping device according to claim 4, wherein the closure gripper is rotatable about a central vertical axis of the closure holder upon coupling the actuator to the passive closure gripper, wherein the actuator comprises a closure-gripper drive for rotating the closure gripper.

9. The decapping/recapping device according to claim 4, further comprising, a closure-holder drive for sequentially and/or repeatedly bringing the plurality of individual closure holders in coupling connection with one or more actuators.

10. The decapping/recapping device according to claim 4, further comprising, a decapping station having a decapping actuator aligned to a decapping tube gripper; and a recapping station having a recapping actuator aligned to a recapping tube gripper, wherein a closure holder and a sample tube are movable from the decapping station, the decapping actuator and the decapping tube gripper cooperate with the passive closure gripper to remove a closure from the sample tube, to the recapping station wherein the recapping actuator and the recapping tube gripper cooperate with the passive closure gripper holding the closure to reclose the sample tube with the same closure.

11. The decapping/recapping device according to claim 4, further comprising, a height determining detector cooperating with the tube gripper for determining a height at which a sample tube is to be lifted when removing a closure from the sample tube or reclosing the sample tube with its closure.

12. The decapping/recapping device according to claim 4, wherein the tube gripper comprises a first tube gripping tool and a second tube gripping tool, wherein the first tube gripping tool is biasable with respect to the second tube gripping tool and cooperates with the second tube gripping tool such that the first tube gripping tool grips and lifts a sample tube from a tube carrier before the second tube gripping tool grips and holds securely the sample tube with a force and a surface of contact greater than the force and surface of contact of the first tube gripping tool respectively.

13. The decapping/recapping device according to claim 4, further comprising, an error detector to determine whether a closure has been removed and/or a sample tube has been reclosed with its respective closure and/or to prevent that a sample tube is reclosed with a non-respective closure.

14. The decapping/recapping device according to claim 4, further comprising, a waste station having a waste actuator aligned to a waste compartment, wherein the waste actuator cooperates with the closure gripper holding the closure to dispose the closure into the waste compartment.

15. A pipetting system for withdrawing volumes of samples from sample tubes and/or dispensing volume of liquids to sample tubes, the pipetting system comprising:

a decapping/recapping device according to claim 4; and a pipetting unit adapted to withdraw a volume of sample and/or dispense a volume of liquid in the time frame between removal of a closure from a sample tube and the reclosing of the sample tube with the same closure.

16. An analytical system for determining at least one sample parameter of a sample contained in a sample tube, the analytical system comprising:

a decapping/recapping device according to claim 4; and an analytical unit for determining the at least one sample parameter in the time frame between removal of a closure from a sample tube and the reclosing of the sample tube with the same closure.

17. A system for processing sample tubes comprising biological samples, the system comprising:

a plurality of work cells for processing samples;

a pipetting system according to claim 15 in correspondence to at least one work cell for withdrawing a volume of sample from a sample tube to be processed by the work cell and/or for dispensing a volume of liquid into a sample tube, for removing a closure from a sample tube when a sample needs to be withdrawn and/or a liquid needs to be dispensed and for reclosing the sample tube before it is transported to another work cell.

* * * * *